US 6,600,556 B2

(12) United States Patent
Green et al.

(10) Patent No.: US 6,600,556 B2
(45) Date of Patent: Jul. 29, 2003

(54) SYSTEM AND METHOD FOR DETECTING MANUFACTURING MARKS ON SPUTTERED DISKS

(75) Inventors: Paul M. Green, Morgan Hill, CA (US); Bob C. Robinson, Hollister, CA (US); Eric Christian O'Brien, Milpitas, CA (US); Elmer Tyree York, San Jose, CA (US)

(73) Assignee: Hitachi Global Storage Technologies Netherlands, B.V., Amsterdam (NL)

( * ) Notice: Subject to any disclaimer, the term of this patent is extended or adjusted under 35 U.S.C. 154(b) by 255 days.

(21) Appl. No.: 09/758,061

(22) Filed: Jan. 10, 2001

(65) Prior Publication Data

US 2002/0089662 A1 Jul. 11, 2002

(51) Int. Cl.$^7$ .......................... G01N 21/00; G01N 21/86
(52) U.S. Cl. ................... 356/237.1; 250/559.44
(58) Field of Search .................... 356/237.1, 237.2, 356/237.3; 250/559.4, 559.44

(56) References Cited

U.S. PATENT DOCUMENTS

| 4,197,011 A | * | 4/1980 | Hudson ....................... 356/521 |
| 4,794,265 A | * | 12/1988 | Quackenbos et al. .. 250/559.45 |
| 4,832,487 A | * | 5/1989 | Mikuriya et al. ........ 356/243.1 |
| 5,037,262 A | * | 8/1991 | Moll et al. ............. 414/222.04 |
| 5,135,303 A | * | 8/1992 | Uto et al. ................ 356/237.2 |
| 5,389,794 A | * | 2/1995 | Allen et al. ............ 250/559.48 |
| 5,762,391 A | * | 6/1998 | Sumnitsch ................ 294/119.1 |
| 5,875,029 A | * | 2/1999 | Jann et al. ................... 356/450 |
| 5,986,761 A | | 11/1999 | Crawforth et al. |
| 6,057,926 A | * | 5/2000 | Horai .......................... 356/430 |
| 6,078,385 A | * | 6/2000 | Yoshiyama et al. ..... 250/559.45 |
| 6,100,971 A | | 8/2000 | Imaino et al. |
| 6,262,432 B1 | * | 7/2001 | Brunfeld et al. ....... 250/559.45 |
| 6,356,346 B1 | * | 3/2002 | Hagen et al. ............ 356/237.1 |
| 6,395,349 B1 | * | 5/2002 | Salamon ..................... 427/555 |

* cited by examiner

Primary Examiner—Zandra V. Smith
Assistant Examiner—Gordon J Stock
(74) Attorney, Agent, or Firm—John L. Rogitz

(57) ABSTRACT

A method for detecting manufacturing marks on sputtered disks includes rotating the disk three hundred and sixty degrees. As the disk rotates, a sensor is used to detect a quantity of manufacturing marks formed on the outer edge of the disk. If there are less than four manufacturing marks on the edge of the disk, a signal is sent to a warning device to indicate that the disk is defective. The lack of a manufacturing mark is an indication that a gripper used to hold the disk within the sputtering chamber during the sputtering process is bent or otherwise misaligned. As such, a signal is also sent to the warning device to indicate that the grippers within the sputtering chamber must be inspected.

16 Claims, 3 Drawing Sheets

SYSTEM AND METHOD FOR DETECTING MANUFACTURING MARKS ON SPUTTERED DISKS

FIELD OF THE INVENTION

The present invention relates generally to computer hard drive disks manufactured using a sputtering process.

DESCRIPTION OF THE RELATED ART

A hard disk drive (HDD) typically includes an array of storage disks from which and to which information is read and written. One commonly used method for manufacturing these disks is a sputtering process in which layers of material, e.g., aluminum and magnesium, are electrically deposited on a thinfilm glass substrate. During the sputtering process, each disk is held at its outer periphery at four points by two grippers. As the material is sputtered onto the disk, the grippers prevent it from being deposited on the outer edge of the disk at the four points of contact. Thus, a properly sputtered disk will have four manufacturing marks, i.e., shadows, around its outer periphery.

If a gripper is bent, it can leave a shadow on the surface of the disk instead of on the outer edge of the disk. Unfortunately, a shadow on the surface of the disk can expose the disk surface to corrosion. This corrosion can interfere with the read/write process resulting in improper operation of the HDD in which an improperly sputtered disk is installed. In light of the above problems, the present invention recognizes a need for a method to detect when a gripper is bent or otherwise misaligned.

SUMMARY OF THE INVENTION

A method for testing a computer disk includes sensing plural manufacturing marks on the disk. Based on the sensing act, a warning device is used to selectively indicate that the disk is defective. In a preferred embodiment, a quantity of manufacturing marks is compared to a predetermined value. If the quantity does not match the value, it is indicated that the disk is defective.

Preferably, the method further includes sensing a size of each manufacturing mark. Based on this sensing act, a warning device is used to selectively indicate that a disk gripper should be inspected. Moreover, the size of each manufacturing mark is compared to a predetermined threshold. If the size of the mark bears a predetermined relationship to the threshold, it is then indicated that the disk gripper should be inspected.

In a preferred embodiment, the disk is manufactured using a sputtering process and the manufacturing marks are shadows on the disk formed during the sputtering process. Specifically, the disk includes an outer edge and the shadows are located on the outer edge of the disk.

In another embodiment a system for testing computer disks includes a spindle and a disk mounted on thereon. The disk includes an outer edge and a sensor is placed in proximity to the outer edge of the disk to sense manufacturing marks formed thereon. A microprocessor is connected to the sensor and includes a program for determining a quantity of manufacturing marks formed on the edge of the disk.

In yet another aspect of the present invention, a method for testing a computer disk that is manufactured using a sputtering process includes rotating the disk at least three hundred and sixty degrees. As the disk is rotated, a quantity of manufacturing marks on the disk is sensed. If the quantity bears a predetermined relationship to a preselected value, it is indicated that the disk is defective.

The present invention will now be described, by way of example, with reference to the accompanying drawings, in which:

DETAILED DESCRIPTION OF THE PREFERRED EMBODIMENTS

Figure 1:
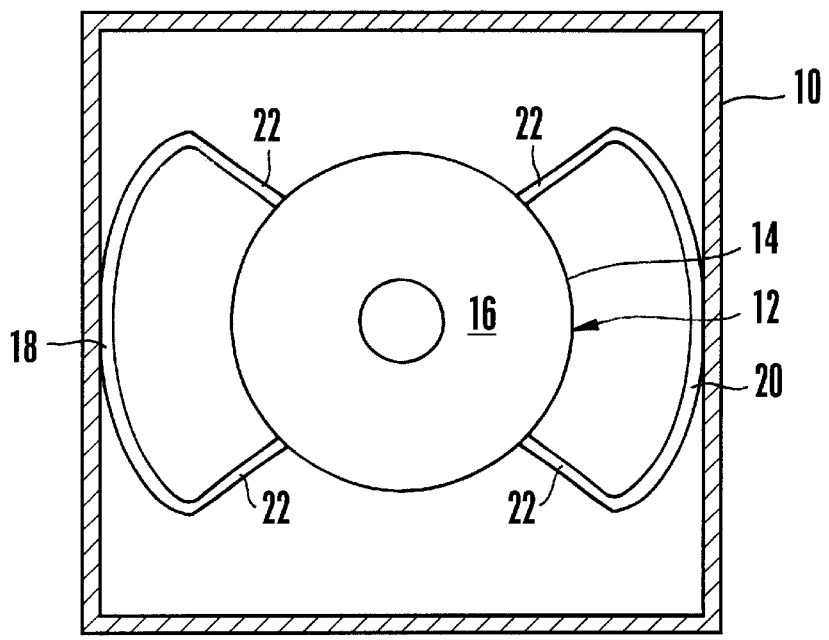
FIG. 1 is a plan view of a disk installed in a sputtering chamber.

Referring initially to FIG. 1, a sputtering chamber is shown and designated 10. Within the sputtering chamber 10 is a disk 12 having an outer edge 14 and a surface 16. Also, within the sputtering chamber 10 is a first gripper 18 and a second gripper 20. Preferably, the grippers 18, 20 are made from spring metal. As shown in FIG. 1, each gripper 18, 20 includes two arms 22 that engage the outer edge 14 of the disk 12 in order to hold the disk 12 firmly within the sputtering chamber 10. As such, there are four contact points between the grippers 18, 20 and the disk 12.

Figure 2:
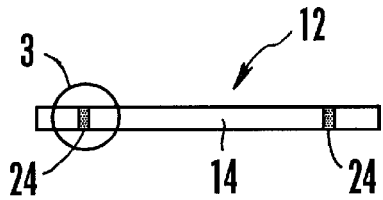
FIG. 2 is a side plan view of a disk.
Figure 3:
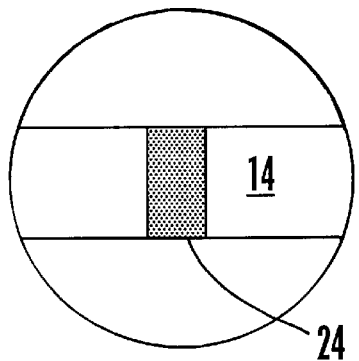
FIG. 3 is a detail view of the disk as indicated by circle 3 in FIG. 2.

As shown in FIGS. 2 and 3, the gripper 18, 20 to disk contact results in the formation of manufacturing marks, i.e., edge shadows 24, on the outer edge 14 of the disk 12. Specifically, during the sputtering process, the gripper arms 22 prevent material from being deposited on the outer edge 14 of the disk 12. This lack of material on the edge 14 of the disk 12 results in the edge shadows 24 shown in FIG. 2. FIG. 2 only shows two edge shadows 24, but it is to be appreciated that a properly sputtered disk 12 will include four edge shadows 24.

FIG. 3 shows a detailed view of an edge shadow 24. As shown in FIG. 3, each edge shadow 24 is essentially a rectangular mark on the edge 14 of the disk 12 where a gripper arm 22 engaged the edge 14 of the disk 12 within the sputtering chamber 10. As described in detail below, these edge shadows 24 can be detected by a sensor to determine if the disk 12 was properly sputtered. The lack of an edge shadow 24 on the disk 12 is a strong indication that a gripper arm 22 is bent and that the disk 12 is defective.

Figure 4:
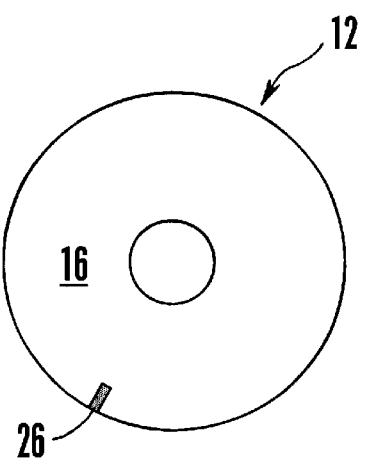
FIG. 4 is a top plan view of a disk with a manufacturing mark formed on the surface of the disk.

As recognized by the present invention, if a gripper arm 22 is bent during the sputtering process, it can partially obscure the surface 16 of the disk 12 and result in the formation of a surface shadow 26 as shown in FIG. 4. The surface shadow 26 forms at the point on the surface 16 of the disk 12 where the bent arm 22 prevents the deposit of material thereon. Such a disk 12 is defective.

Figure 5:
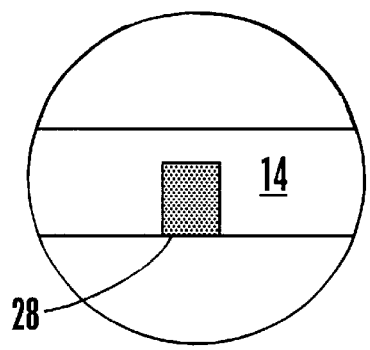
FIG. 5 is a plan view of a partial manufacturing mark.

As further recognized herein, if a gripper arm 22 is not bent to the extent that it obscures the surface 16 of the disk, it nonetheless may be bent as to only partially engage the edge 14 of the disk 12. This partial engagement of the gripper arm 22 with the disk 12 results in a partial edge shadow 28 on the edge 14 of the disk 12 as shown in FIG. 5. As described in detail below, this partial edge shadow 28 indicates that the grippers 18, 20 need to be inspected before the arm 22 in question is bent to the extent that it will obscure the surface 16 of the disk 12 during the sputtering process.

Figure 6:
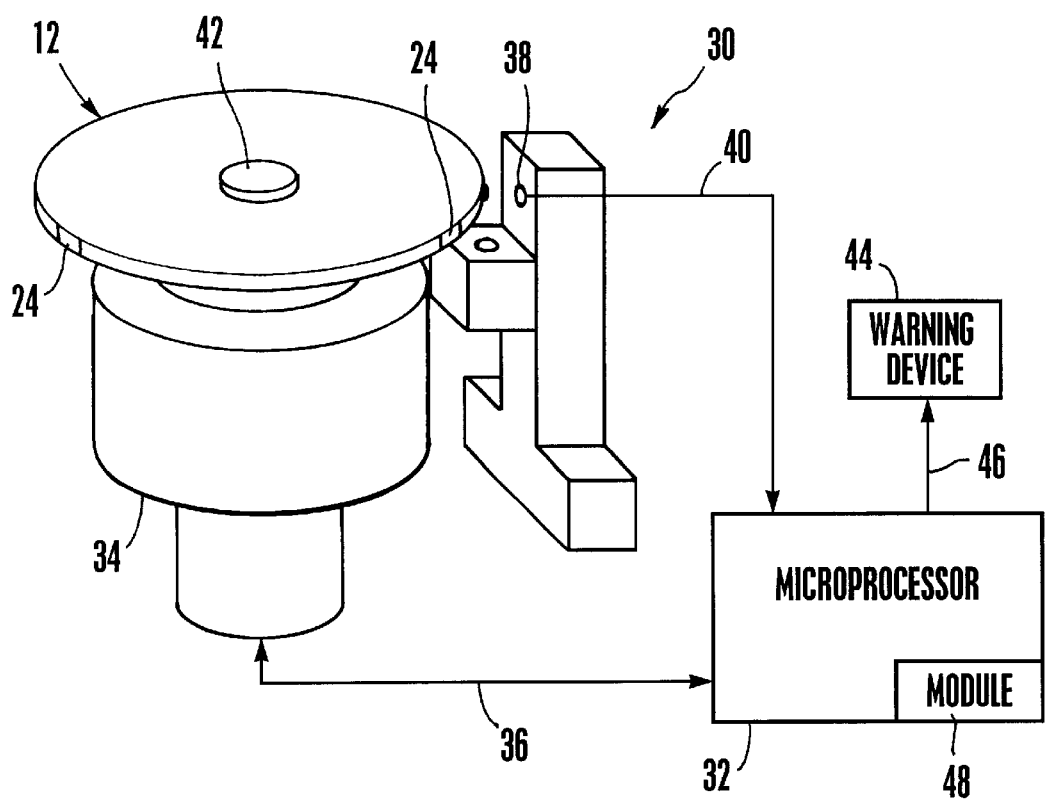
FIG. 6 is a block diagram of a system for testing disks.

Referring now to FIG. 6, a disk test system is shown and generally designated 30. As shown in FIG. 6, the disk test system 30 includes a microprocessor 32 to which a motor 34 is connected via electric line 36. FIG. 6 also shows a sensor 38 that is connected to the microprocessor 32 via electric line 40. As shown in FIG. 6, the motor 34 includes a spindle 42 that rotates when the motor 34 is energized in response to a signal from the microprocessor 32. A disk, such as the type described above, is mounted on the spindle 42. As the spindle 42 rotates, so does the disk 12. The sensor 38 is placed such that it can sense the edge 14 of the disk 12 as it rotates with the spindle 42. As the disk 12 is rotated, the sensor 38 detects the edge shadows 24, 28 formed on the edge 14 of the disk 12 and sends signals to the microprocessor 32 representative of the edge shadows 24, 28. In a preferred embodiment, the sensor 38 is an infrared sensor, but it is to be appreciated that any optical sensor can be used. It is to be further understood that more than one microprocessor 32 can be used to undertake the functions of the system 30.

As shown in FIG. 6, a warning device 44 is connected to the microprocessor 32 via electric line 46. It is to be appreciated that the warning device 44 can be any audible warning device, e.g. a buzzer, that can be used, as described below, to alert an operator of the test system 30 that the disk 12 is defective. On the other hand, it is to be appreciated that the warning device 44 can be any visible warning device, e.g., a lamp, that can be used to alert the operator when a disk 12 is defective. Or, the warning device 44 can be a software module 48 to store data indicating a defect and/or to control the operation of the microprocessor 32 by interacting with the software module 48, as described further below.

The method for detecting the manufacturing marks 24, 28 on the edge of the disk 12, disclosed below, may be executed as a series of instructions by the microprocessor 32. These instructions may reside, for example, in the module 48 of the microprocessor 32, which, when programmed with the present logic, establishes a computer program product.

Alternatively, the instructions may be contained on a data storage device with a computer readable medium, such as a computer diskette having a data storage medium holding computer program code elements. Or, the instructions may be stored on a DASD array, magnetic tape, conventional hard disk drive, electronic read-only memory, optical storage device, or other appropriate data storage device. In an illustrative embodiment of the invention, the computer-executable instructions may be lines of compiled C++ compatible code. As yet another equivalent alternative, the logic can be embedded in an application specific integrated circuit (ASIC) chip or other electronic circuitry.

Figure 7:
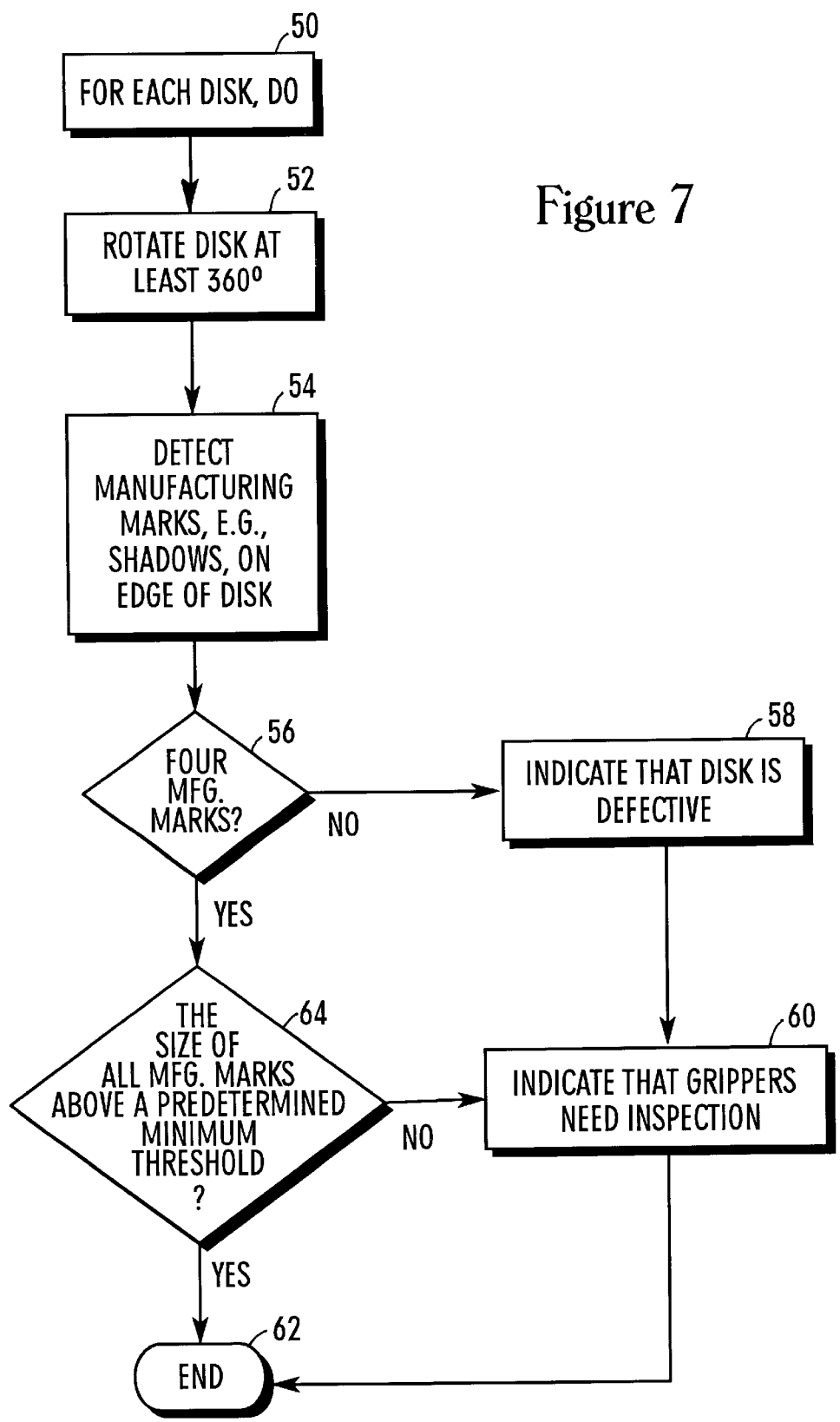
FIG. 7 is a flow chart representing the manufacturing mark detection logic.

Referring now to FIG. 7, the manufacturing mark detection logic of the present invention can be seen. Commencing at block 50, a do loop is entered wherein for each disk 12, the succeeding steps are performed. At block 52, the disk 12 is rotated at least three hundred and sixty degrees (360°), i.e., one revolution. It is to be appreciated that to increase the accuracy of the detection logic, die disk 12 can be rotated through multiple revolutions.

Continuing the description of the logic, at block 54 the manufacturing marks 24, 28 on the edge 14 of the disk 16 are detected using the sensor 38 as the disk 12 is rotated. Proceeding to decision diamond 56, it is determined whether or not the edge 14 of the disk 16 includes four manufacturing marks 24, 26. If not, the logic moves to block 58 where it is indicated to an operator of the test system 30 that the disk 12 is defective. The logic then continues to block 60 where it is indicated that the grippers 18, 20 should be inspected to determine if any of the arms 22 are bent. Thereafter, the logic ends at state 62.

If, at decision diamond 56, four manufacturing marks 24, 28 are detected, the logic proceeds to decision diamond 64 where it is determined if the size of all manufacturing marks, i.e., the height, is above a predetermined minimum threshold. If not, the logic moves to block 60 to indicate that the grippers 18, 20 should be inspected. The logic then proceeds as described above. If the size of each manufacturing mark 24, 28 is above the predetermined minimum threshold, the logic ends at state 62. It is to be understood that the size of the manufacturing marks 24, 28 can be determined by the amplitude of the signal received from the sensor 38.

With the configuration of structure described above, it is to be appreciated that the system and method for detecting manufacturing marks on sputtered disks provides a means by which it can be determined if the grippers 18, 20 are bent or otherwise misaligned within the sputtering chamber 10. Thus, the manufacture of defective disks is reduced or eliminated.

While the particular SYSTEM AND METHOD FOR DETECTING MANUFACTURING MARKS ON SPUTTERED DISKS as herein shown and described in detail is fully capable of attaining the above-described objects of the invention, it is to be understood that it is the presently preferred embodiment of the present invention and thus, is representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it is to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. section 112, sixth paragraph, unless the element is expressly recited using the phrase "means for."

We claim:

1. A method for testing a computer hard drive disk comprising the acts of:

sensing plural in manufacturing marks on the disk;

comparing a quantity of manufacturing marks to a predetermined value; and indicating that the disk defective if the quantity is less than the value.

2. A method for testing a computer hard drive disk comprising the acts of:

sensing plural manufacturing marks on the disk;

sensing a size of each manufacturing mark; and at least partially based on the sensing act, selectively indicating that a disk gripper should be inspected.

3. The method of claim 2, further comprising the acts of:

comparing the size of each manufacturing mark to a predetermined threshold; and indicating that the disk gripper should be inspected if a size of a mark bears a predetermined relationship to the threshold.

4. A system for testing computer hard drive disks, comprising:

at least one spindle;

at least one disk mounted on the spindle, the disk having an outer edge;

at least one sensor placed in proximity to the outer edge of the disk to sense manufacturing marks; and at least one microprocessor for connected to the sensor, the microprocessor including a program for determining at least one of:

a quantity of manufacturing marks formed on the edge of the disk, and a size of at least one of said marks, the microprocessor outputting a signal representative of a defect if at least one of:

the quantity is less than a predetermined quantity, and the size is less predetermined size is determined to exist.

5. The system of claim 4, wherein the program includes:

logic means for sensing the quantity of manufacturing marks on the disk as the disk rotates; and logic means for indicating that the disk is defective at least partially based on the means for sensing.

6. The system of claim 5, further comprising:

logic means for comparing the quantity of manufacturing marks to a predetermined value; and logic means far indicating that the disk is defective at least partially based on the means for comparing.

7. The system of claim 5, farther comprising:

logic means for sensing a size of each manufacturing mark; and logic means for selectively indicating that a disk gripper should be inspected at least partially based on the sensing means.

8. The system of claim 7, further comprising:

logic means for comparing the size of each manufacturing mark to a predetermined threshold; and logic means for indicating that the disk gripper should be inspected if the size of at least one manufacturing mark bears a predetermined relationship to the threshold.

9. The system of claim 4, wherein the disk is manufactured using a sputtering process and the manufacturing marks are shadows on the disk formed during the sputtering process.

10. The system of claim 9, wherein the disk includes an outer edge and the shadows are located on the outer edge of the disk.

11. A method far testing a computer disk manufactured using a sputtering process, comprising the acts of:

sensing a quantity of manufacturing marks on the disk; and indicating that the disk is defective if the quantity bears a predetermined relationship to a preselected value, the predetermined relationship being that the quantity is less than preselected value.

12. The method of claim 11, further comprising the act of:

at least partially based on the sensing act, indicating that a gripper used to hold the disk while it is sputtered should be inspected.

13. The method of claim 11, further comprising the acts of:

sensing a size of each manufacturing mark; and at least partially base on the sensing act, selectively indicating that a disk gripper should be inspected.

14. The method of claim 13, further comprising the acts of:

comparing the size of each manufacturing mark to a predetermined threshold; and indicating that the disk gripper should be inspected if the size of at least one manufacturing mark bears a predetermined relationship to the threshold.

15. The method of claim 11, wherein the disk is manufactured using a sputtering process and the manufacturing marks are shadows on the disk formed during the sputtering process.

16. The method of claim 15, wherein the disk includes an outer edge and the shadows are located on the outer edge of the disk.

* * * * *